United States Patent [19]

Matthews et al.

[11] Patent Number: 4,834,105
[45] Date of Patent: May 30, 1989

[54] CALIBRATION METHOD AND APPARATUS FOR TONOMETERS

[75] Inventors: James R. A. Matthews, Old Windsor; Mervyn A. Little, Cambereley; John Fisher, Royston, all of England

[73] Assignee: Keeler Limited, Berks, England

[21] Appl. No.: 118,159

[22] Filed: Nov. 9, 1987

[30] Foreign Application Priority Data

Nov. 7, 1986 [GB] United Kingdom ............... 8626601

[51] Int. Cl.4 .............................................. A61B 3/16
[52] U.S. Cl. .................................................. 128/648
[58] Field of Search ...................... 128/648, 652, 645

[56] References Cited

U.S. PATENT DOCUMENTS

| 3,585,849 | 6/1971 | Grolman | 128/648 |
| 3,832,890 | 9/1974 | Grolman et al. | 128/648 |
| 4,665,923 | 5/1987 | Kobayashi | 128/648 |
| 4,705,045 | 11/1987 | Nishimura | 128/648 |
| 4,724,843 | 2/1988 | Fisher | 128/648 |

FOREIGN PATENT DOCUMENTS 183621 6/1986 European Pat. Off. ............ 128/648

*Primary Examiner*—Edward M. Coven
*Attorney, Agent, or Firm*—Oblon, Fisher, Spivak, McClelland & Maier

[57] ABSTRACT

A tonometer is described for measuring the intra-ocular pressure of an eye in which a pulse of fluid is projected towards the cornea of the eye to distort the corneal surface by the pressure of the pulse, the distortion in the corneal surface being detected by a change in the reflection of light directed onto the cornea. A fluid delivery system (36, 44, 48) leads to an outlet through which the fluid pulse is applied to the cornea, and a branch (54) leads to a pressure measuring chamber (52), containing a transducer (170) which produces an electrical signal whose value depends on the pressure in the branch. A flow restrictor is removably fitted in the branch (54) and signal processing means (176, 178, 180) (the gain and rise time of which are adjustable by (182) or (186)), is supplied with the output from the transducer. Adjustment of 182, and 186 enable the electrical signal output of the processing means to be adjusted, for calibration. Calibration of the instrument is achieved by selecting an appropriately dimensioned restrictor and by adjusting the gain, and where appropriate the time constant, of the signal processing means, so that the plot of a pressure-time signal curve of the processing means output corresponds to the pressure-time curve for such an instrument when set to operate in line with a clinical standard.

11 Claims, 8 Drawing Sheets

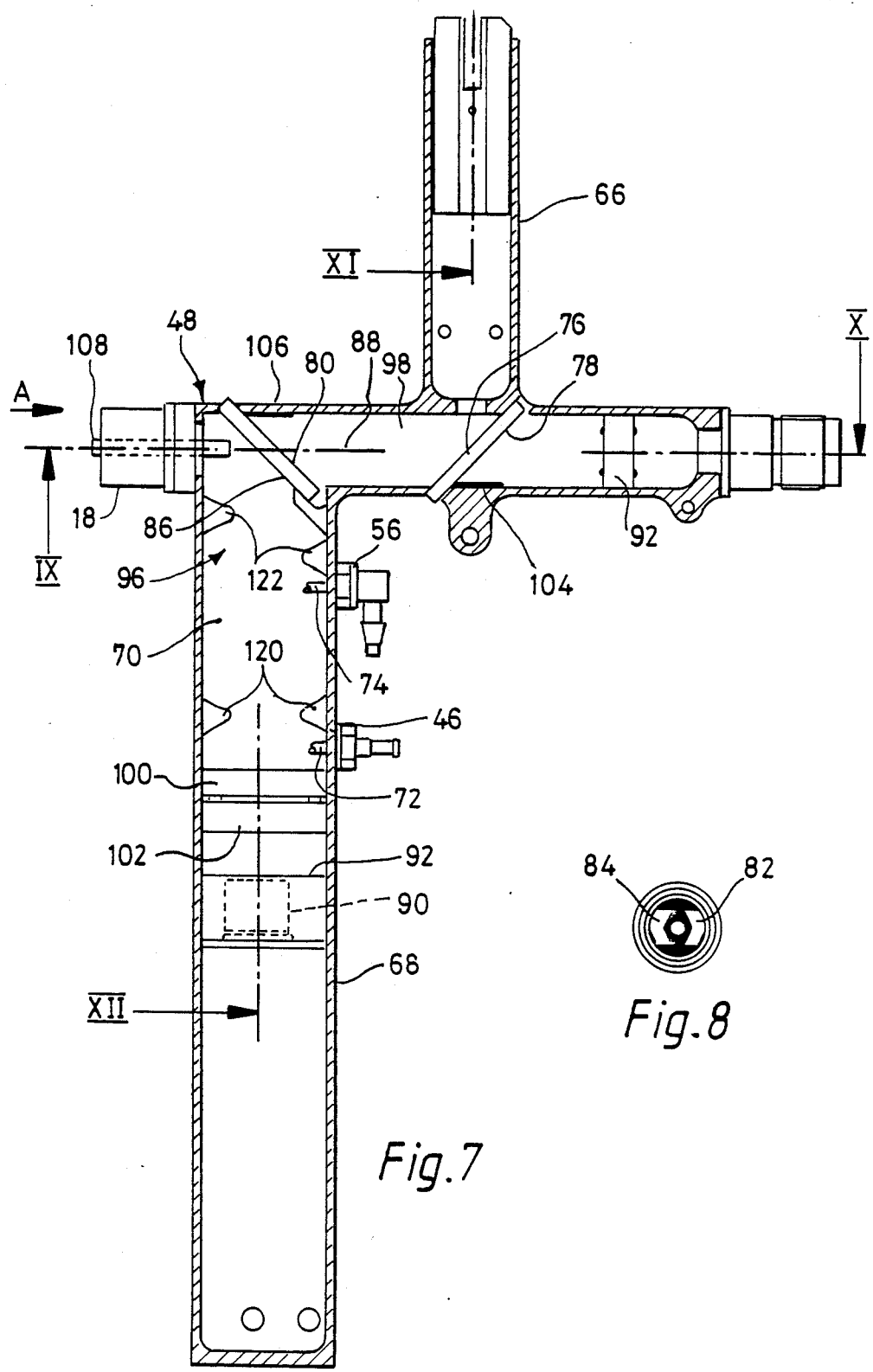

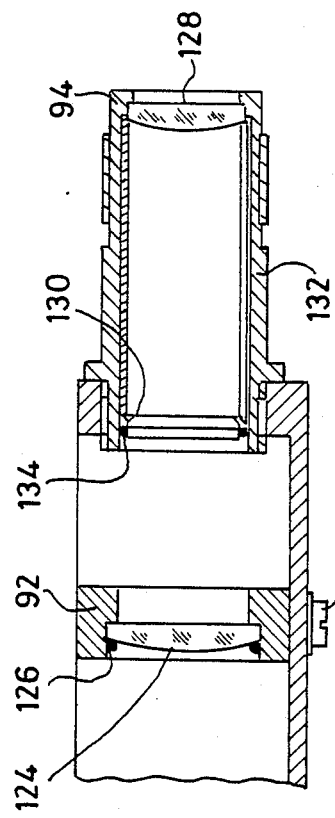
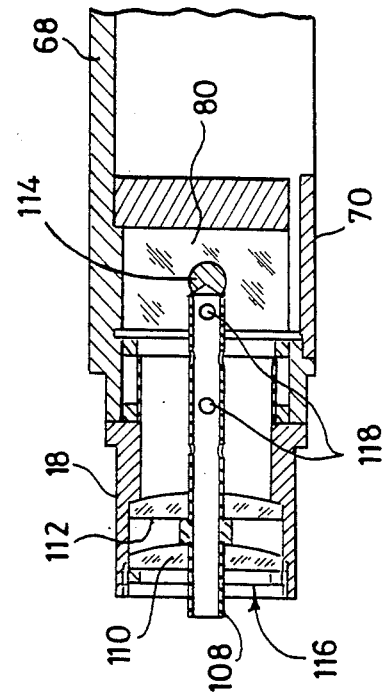
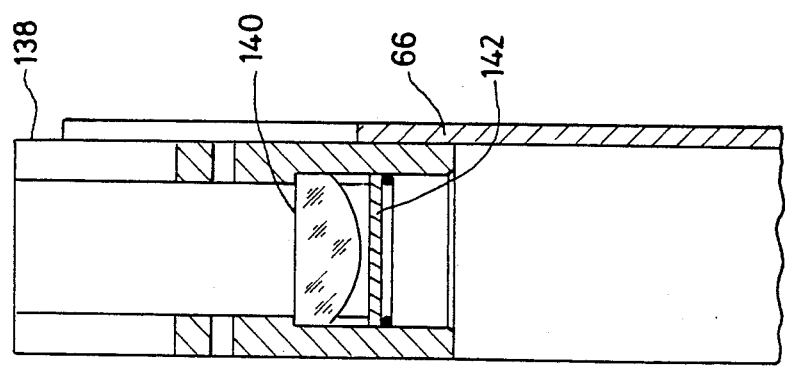

CALIBRATION METHOD AND APPARATUS FOR TONOMETERS

FIELD OF INVENTION

This invention relates to a tonometer of the non contact type for measuring the intra-ocular pressure of an eye.

BACKGROUND TO THE INVENTION

British Patent Specification No. 2,175,412 corresponding to U.S. patent application Ser. No. 07/225,718 filed on July 23, 1988 describes an improved form of non contact tonometer and methods of use.

It is an object of the invention to provide means whereby such a tonometer can be calibrated to a particular standard and certain improvements in the construction of the tonometer described in the aforementioned specification.

SUMMARY OF THE INVENTION

According to the present invention there is provided a tonometer for measuring the intra-ocular pressure of an eye in which a pulse of fluid is projected towards the cornea of the eye to distort the corneal surface by the pressure of the pulse, the distortion in the corneal surface being detected by a change in the reflection of light directed onto the cornea characterised by:

(1) a fluid delivery system leading to an outlet through which the fluid pulse is applied to the cornea, (2) a branch in the fluid delivery system which leads to a pressure measuring chamber, (3) a transducer in the chamber which produces an electrical signal whose value depends on the pressure in the branch, (4) a fluid flow restrictor in the branch leading to the transducer, and (5) signal processing means the gain and rise time of which are adjustable, to enable the electrical signal output of the processing means to be adjusted, for calibration.

A first step in calibration is achieved by selecting the size of the aperture and/or the length of the bore of the fluid flow restrictor, or adjusting one or both of these dimensions of the fluid flow restrictor.

The signal processing means may comprise an analogue amplifier the gain and time constant of which re adjustable and an analogue to digital converter, to which the amplifier output is supplied, wherein adjustment of the gain enables the amplitude and variation of the time constant enables the rise time, of the signal supplied to the analogue to digital converter to be adjusted.

Adjustment of the gain and/or time constant of the signal processing means provides the second step in the calibration of the tonometer.

It is to be understood that calibration may be achieved entirely by adjustment of the dimensions of the fluid flow restrictor or by adjusting the parameters of the signal processing means, or a continuation of both adjustments.

The fluid delivery system may include a housing having at one end an apertured lens comprising the said outlet for the fluid pulses, inlet means to which fluid under pressure can be supplied when a pulse is required, and a connection for the said branch leading to the pressure measuring transducer.

The housing may include a first section which extends between the lens at the one end and a viewing eyepiece at the other and may accommodate a source of illumination, and an optical focussing and reflecting system.

The housing may include a second section within which the source of illumination is located.

The housing may include a third section containing light detection means on which light reflected from an eye under test can be focussed, the fluid inlet means and the connection to the said branch leading to the pressure meaning transducer.

One part of the housing comprising said third section and a portion of the first section leading from the third section to the apertured lens preferably comprise one part of the housing which is separated from the remainder of the housing by means of a semi-reflecting mirror fitted so as to represent fluid-tight seal between the said one part and the remainder of the housing.

At least a part of the wall of the housing may be comprised of a printed circuit board forming at least a light tight seal with the housing, and electrical components required to be located within the housing are mounted on regions of the printed circuit board which communicate directly with the interior thereof.

The apertured lens preferable comprises a pair of aligned centrally apertured plano-convex lenses and a tube extends through the aligned apertures in the lenses, and a mask which determines the light pattern which is to form the final image on the light detection means is formed on one of the plane surfaces of the lenses.

The mask may comprise two slit like windows symmetrically arranged relative to the central opening and bounded by an opaque surround.

Calibration of the instrument is possible by selecting an appropriately dimensioned restrictor for feeding the air pressure to the transducer and by adjusting the gain, and where appropriate the time constant, of the amplifier in the signal processing means, so that a pressure-time signal curve produced by the amplifier corresponds as closely as possible to pressure time curve for such an instrument when set to operate in line with a clinical standard, typically the Goldmann instrument standard In order to set up a calibration station, a specimen instrument constructed in accordance with the invention is first calibrated so as to produce results which are a close approximation to those which would be obtained from a standard instrument such as a Goldmann instrument. This is achieved using clinical trials involving the specimen instrument and a standard Goldman instrument and by comparing the results obtained from the trials. Adjustment of the specimen instrument is made until the results from the two instruments are compatible within the degree of accuracy required.

The specimen instrument is then said to be calibrated according to the standard and can be used to set up a calibration station for the calibration of future instruments.

The station essentially comprises means for supporting an instrument under test a fixed distance away from a test pressure transducer, and electrical circuit means responsive to signals from the test pressure transducer to generate an electrical analogue signal corresponding to the pulse of air pressure applied thereto from an instrument under test. The pressure transducer within the instrument under test also generates an electrical analogue signal in response to rising pressure within the instrument chamber, and the test station provides for the comparison of the electrical signal obtained from the transducer within the instrument undertest with the signal obtained from the test transducer, by the supply of the two signals to a double beam oscilloscope having signal storage facility. This enables two traces to be displayed corresponding to the two analogue signals obtained during the release of a pulse of air from an instrument under test, to enable the observer to check on identity of amplitude and phase.

A calibration procedure using such a test station comprises the following steps:

1. locate the instrument to be calibrated a fixed distance from a test pressure transducer, which has previously been calibrated using a specimen instrument which itself has been calibrated in clinical trials involving a Goldmann standard instrument, or the like, as the reference, 2. using a double beam oscilloscope having signal storage facility, simultaneously plot the instantaneous electrical signal values produced by the analogue circuits associated with the pressure transducer within the instrument under test and the analogue signal from the test transducer against a time axis, during the release of a single pulse of air from the instrument under test, 3. compare the two curves so obtained on the oscilloscope and adjust the gain and time constant of the signal processing means of the instrument under test, so as to correct the curve produced by the signals from the transducer within the instrument under test, to more closely approximate to the curve from the test transducer, and 4. repeat the comparison and adjustment until a desired level of identity between the pressure/time curves is obtained.

The invention will now be described by way of example, with reference to the accompanying drawings in which:

FIG. 7 is a side view of the housing containing the optical elements of the tonometer to an enlarged scale;

FIG. 8 is a view in the direction of the arrow A, and indicates the object pattern;

FIG. 9 is a cross-sectional view through the puff tube end of the housing of FIG. 7;

FIG. 10 is a cross-sectional view through the eyepiece end of the housing of FIG. 7;

FIG. 11 is a cross-section through the lamp holder end of the housing of FIG. 7;

DETAILED DESCRIPTION OF THE DRAWINGS

Figure 1:
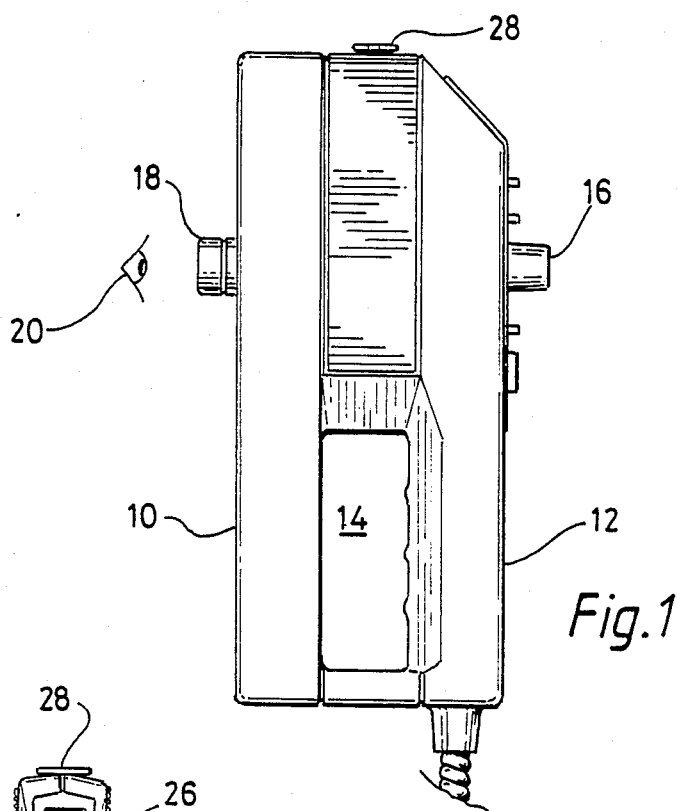
FIG. 1 is a side view of a hand held tonometer constructed in accordance with the invention.
Figure 2:
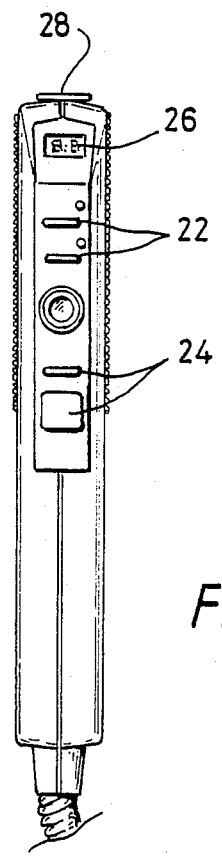
FIG. 2 is a front view of the tonometer of FIG. 1.
Figure 3:
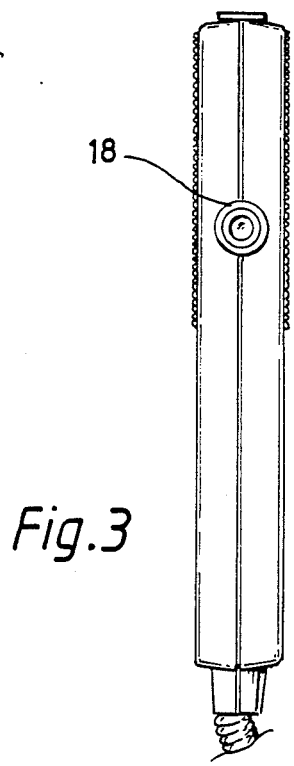
FIG. 3 is a rear view of the tonometer shown in FIG. 1.

FIGS. 1, 2 and 3 show three views of a hand held tonometer embodying the invention. This comprises a casing generally designated 10 having a handgrip section 12 and a cut-out 14 through which the fingers of one hand can be inserted whilst grasping the handgrip section 12. The unit includes an eyepiece 16 and an inspection lens 18 which includes centrally an outlet for air pulses to be applied to an eye under test. The latter is shown diagrammatically at 20.

The user holds the instrument in the left or right hand and looks through the eyepiece 16 whilst positioning the unit all as described in our earlier application No. 8611901 to be published under Ser. No. 2175412.

On the rear of the unit are located various push-button switches such as 22 and 24 and a digital display device 26 for indicating a numerical value attributable to the intra occular pressure of the eye under test.

On the top of the unit can be seen the cap or cover 28 associated with the lamp housing to be described later.

Figure 4:
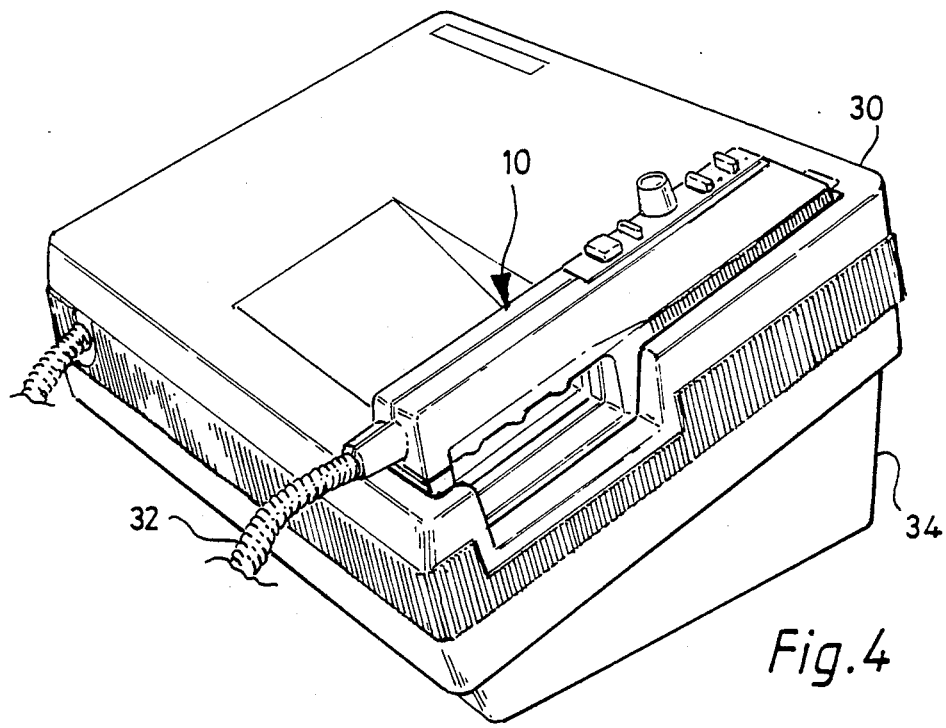
FIG. 4 is a perspective view showing the hand held tonometer installed in a base unit adapted to be placed on a horizontal surface such as a desk.

A base unit is provided into which the hand held unit can be fitted in use. The base unit includes a tilted upper section 30 which in the form shown in FIG. 4 provides that the handgrip section 12 is lower than the other end of the hand held unit when the latter is in position. The hand held unit is connected to the base unit via an umbilical cord 32 which houses an air line and electrical power cables as required.

Figure 5:
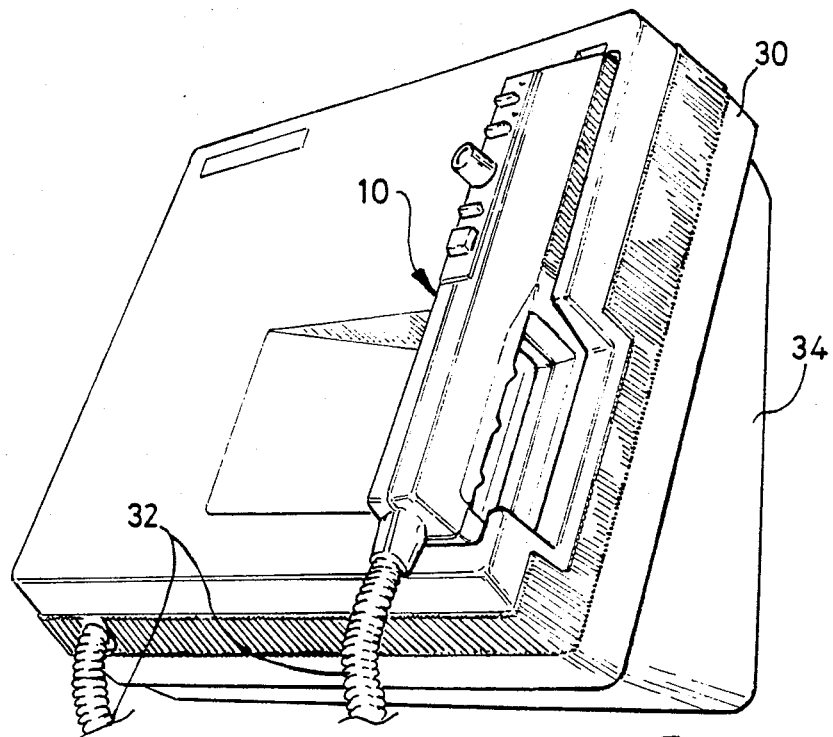
FIG. 5 is a perspective view of the hand held unit installed in a similar base unit but this time adapted for wall mounting.

In some situations it is preferable that the base unit be mounted on wall and to this end the lower part of the housing 34 can be removed from the upper part and rotated through 180° so that if then mounted on a vertical surface such as a wall, the upper part of the housing is now inclined in a manner so as to receive and support the unit 10 as shown in FIG. 5. In this mode the base unit can be thought of as a holster.

Figure 6:
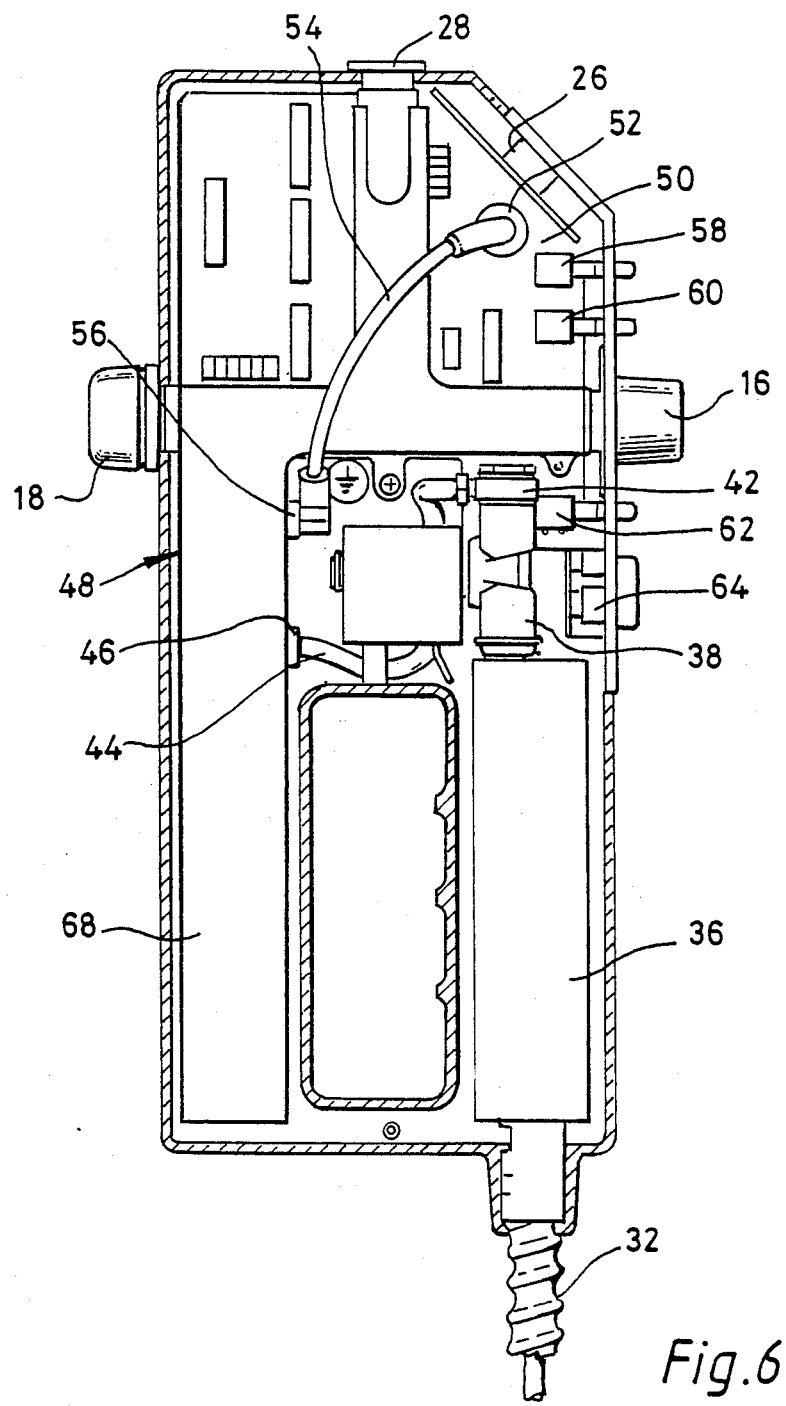
FIG. 6 is a side view of the unit shown in FIG. 1 with the nearside cover removed.

FIG. 6 illustrates the interior of the hand held unit which is revealed by the removal of the nearside casing of the unit 10 as shown in FIG. 1. Inside, the umbilical cord communicates with an air reservoir 36, an outlet of which is connected to the inlet of an air valve 38. The latter is solenoid operated, the solenoid being housed in housing 40 and the valve is normally closed. The outlet part of the valve 42 communicates via a tube 44 with an inlet 46 to a plenum chamber (not shown in FIG. 6) contained within the housing generally designated 48.

As will be described later, air from the plenum chamber escapes through a small orifice in the inspection lens 18. The pressure of the air in the plenum chamber is sensed by a pressure transducer located on a printed circuit board 50 and covered by a cylindrical housing 52 which itself communicates with the plenum chamber via a tube 54. The other end of the tube 54 is connected to an outlet 56 which extends through the wall of the plenum chamber in the housing 48.

Switches such as 58, 60, 62 and 64 are mounted on the printed circuit board 50 and have actuating buttons which protrude through the casing of the housing 10 as shown in FIGS. 1 and 2. Also visible in FIG. 6 is a two-digit digital display device 26 referred to in relation to FIG. 2.

The housing 48 includes a horizontal section which extends from the eyepiece 16 to the inspection lens 18, an upright limb designated 66 at the upper end of which is housed a lamp (to be described in more detail later) and a lower limb designated 68 which largely houses the plenum chamber—also to be described later.

The housing 48 can be seen in more detail in FIG. 7 which is a cross-sectional view through the housing. In the region of the plenum chamber a coverplate 70 is fitted on the underside of the housing.

Thus the air inlet 46 is shown protruding into the plenum chamber at 72 and the air outlet for feeding the pressure transducer is shown with a protruding pipe 74.

The housing contains a lamp which protrudes into the upper limb 66 and includes a cap or cover plate 28 by which the lamp can be withdrawn for replacement or cleaning. The lamp is typically held in position by means of a bayonet or screw thread as is also the cap 28.

Light from the lamp is reflected by the upper surface 76 of a first semi-reflecting mirror 78 located at an angle of 45° to the axis of the limb 66 and likewise at 45° to the axis of the central limb of the housing 48. Light is reflected towards and through a second semi-reflecting mirror 80 and illuminates an object which is located in the inspection lens assembly 18 and if viewed in the direction of arrow A will appear as shown in FIG. 8. Thus the only light which passes is that which is incident on the two shallow V shaped windows 82 and 84 and it is a pattern of those two windows which is formed on the eye and is reflected back through the inspection lens assembly 18. Some of the light incident on the lower surface 86 of the second semi-reflecting mirror 80 is reflected at right-angles to the axis 88 and after passing through a lens and transparent windows (to be described), is reflected by an inclined mirror 90 shown in dotted outline in FIG. 7, since it is located on an inclined face of a supporting plate 92 located within the housing limb 68.

Figure 12:
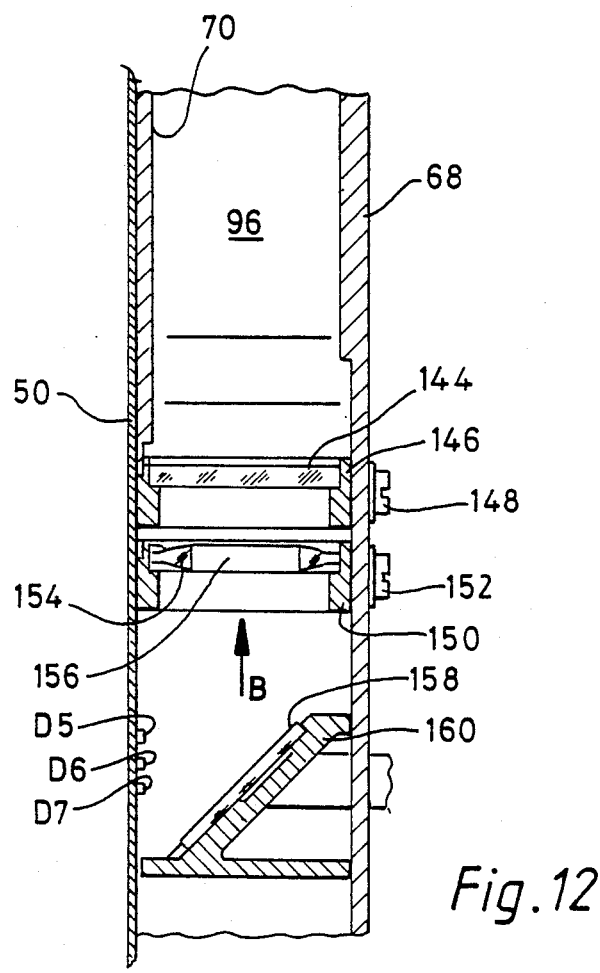
FIG. 12 is a cross-section through the lower limb of the housing shown in FIG. 7.

Light from the mirror 90 is reflected onto three photodiodes (shown in more detail in FIG. 12).

Light not reflected in this way by the lower surface 86 of the second semi-reflecting mirror 80, passes along the axis 88, through the semi-reflecting mirror 78 and after passing through a lens located in a lens mount 92 and a second lens mounted in the eyepiece 94, can be viewed by the observer.

The semi-reflecting mirror 80 may be cemented in position so as to completely close off the region 96 from the region 98 within the housing 48, but as will be described later, this is not the case in the embodiment as shown, and the air tight seal is instead provided around the optical element beyond the mirror 80 as will be described.

At the lower end of the plenum chamber 96 a glass plate 100 completely seals off the chamber the lower section of the limb 68 of the housing.

A constraint lens 102 is located below the glass plate 100.

In order to cut down on unwanted light reflectance, pads of black cotton velvet are located in the region of the semi-reflecting mirrors 78 and 80, at 104 and 106 respectively. The pad 104 absorbs any light which passes through the semi-reflecting mirror 80 and which if not absorbed might be reflected and would cause unwanted light in the optical system. Similarly the pad 106 is placed below the semi-reflecting mirror 80 to absorb any light passing through the latter after it has been reflected by the eye under test, together with any light reflected off the top surface at right angles to the main beam.

It is to be noted that the use of the two shallow V-shaped windows in the mask puts the light at the extremities of the apertures which introduces greater than usual problems with reflection from the surfaces of lenses and mirrors since the light is no longer concentrated along the optical axis as would normally be the case in conventional optical systems.

FIG. 9 is a cross-section on the optical axis of the housing 48 and shows the outlet from the plenum chamber (for feeding the pulses of air towards the eye under test) as comprising a tube 108 which protrudes centrally through two lenses 110 and 112 one of which has on its plane surface the mask shown in FIG. 8. The tube protrudes rearwardly into the plenum chamber where its inward end is closed at 114. Air can pass into the tube 108 via a series of apertures such as 116 and 118 which are formed in the wall of the tube beyond the second lens 112.

It is found in practice that by aperturing the wall of the tube in this way the length of the tube protruding into the plenum chamber is less critical than if an ordinary open-ended tube is used, where it is now well established that the inwardly protruding length must be accurately determined if optimum performance is to be obtained.

The provision of an apertured tube 108 thus has a distinct advantage over the use of a single open-ended tube since a further tight manufacturing tolerance has been removed from the assembly of the instrument.

Operation of the apertured tube 108 leading from the plenum chamber is believed to be as follows.

The distributed mass and distributed elasticity of the air in the plenum chamber have time constants which are not negligibly short compared with the charging time of the plenum chamber. This arises from the fact that the plenum chamber is itself supplied through a relatively small bore tube. Thus oscillations and possibly turbulance arise within the plenum chamber so that at any instant there may be different pressures in different parts thereof. Whilst it may be possible by careful design of the chamber to select one particular point within the chamber at which the effects of oscillation and/or possibly turbulance are at a minimum, and to locate the entry to a single apertured puff tube at that point the provision of a series of apertures produces an arrangement which is tolerant of manufacturing variations and does not require accurate adjustment to locate any one particular aperture at a point of minimal disturbance within the chamber as is characteristic of other designs.

Reverting to FIG. 7, the coverplate 70 is secured by means of screws or other fixings to two pairs of lugs shown at 120, 122, and this coverplate 70 can be seen in FIG. 9.

Referring back to FIG. 8, the mask defining the two V shaped windows 82 and 84 may be formed on the plane surface of the plano-convex lens 110 or 112. A protective glass window 116 fits over the open end of the tube 118 within which the lenses are housed and serves to protect the lens 110.

To the rear of the tube 108 i located the half silvered mirror or beam splitter 80 shown in FIG. 7, the half silvered mirror being cut and revealing its cross-section by virtue of the cross-sectional view.

As shown in FIG. 9, the mirror is secured along one edge to the inside of the closed wall of the housing 48 but there is a clearance between its opposite edge and the underside of the coverplate 70 fitted over the open face of the housing 48. This means that air can escape past the half silvered mirror 80 into the region 98 (see FIG. 7) and to this end either the half silvered mirror 78 must be made a good air-tight fit across the housing or an air tight seal must be formed around the lens and lens mounting 92 to prevent the loss of air pressure at that end of the housing. Likewise, the lamp holder must be made a good air-tight fit within the limb 66.

FIG. 10 indicates in detail the construction of the lens mount 92 and the eyepiece generally designated 94. A plano-convex lens 124 is mounted within the lens mounting 92 and a seal 126 is provided around the periphery of the lens between it and the lens mount 92 to provide the air tight seal should this be required.

The eyepiece 94 is of fixed focal length and includes at its far end a second plano-convex lens 128. A window is formed at 130 at the inboard end of the tubular member 132 housing the lens 128, and a seal 134 is provided in the region of the window 130 to prevent the loss of air pressure should the seal 126 fail.

In addition to preventing the loss of air pressure, the air-tight seals provided within the instrument also prevent the ingress of dirt and moisture into the housing.

As shown in FIG. 10, the lens mount 92 is secured in position by means of one or more screws as at 136.

FIG. 11 gives detail of the lens associated with the lamp holder. The latter is in the form of a sleeve 138 which itself is an air-tight fit within the limb 66 of the housing 48. At the lower end of the sleeve 138 is a plano-convex lens 140 below which is located a transparent window 142 which is fitted with an air-tight seal within the interior of the tube 138. A lamp holder (not shown) can be slid into the sleeve 138 and located in position above the lens 140 and preferably a lens of very accurate dimensions with an accurately centred filament is employed so as to provide good uniform illumination from the condensing lens 140.

FIG. 12 shows in more detail the central region of the limb 68 of FIG. 7 which defines the lower extremity of the plenum chamber 96. The latter is closed off by means of a plate glass window 144 which is secured within a window frame 146, itself secured in position by one or more screws as at 148. Immediately therebelow is a lens mounting 150 secured in position by means again of one or more screws 152. A convex lens 154 is located within the lens mount 150. The central region of the lens has been removed as will be seen from FIG. 12 to leave a central circular aperture 156. The operation of the lens is as described in our aforementioned patent application.

Figure 13:
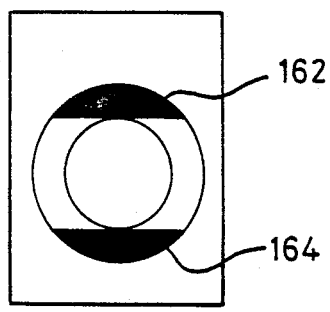
FIG. 13 is a view in the direction of arrow B in FIG. 12.

Formed on opposite regions of the lens or on the window are two marking strips as shown in FIG. 13 so that if viewed in the direction of arrow B in FIG. 12, the top and bottom regions of the lens are completely opaque.

Immediately below the lens is situated an inclined mirror 158 carried by a support 160. The latter extends across the interior of the housing limb 96 and supports the mirror 158 at 45° to the axis of the limb.

Whilst the plate 70 closes off limbs to define the plenum chamber, the face of the limb below the lens 154, is open thereby allowing three photodiodes D5, D6 and D7 mounted on a printed circuit board 50 to protrude into the interior of the limb to receive light directly from the mirror 158. The housing is positioned relative to the printed circuit board so that the diodes D5, D6 and D7 are at the correct point to receive the light from the mirror 158 so that when the instrument is correctly positioned relative to an eye under examination, the two outer diodes D5 and D7 receive light from the two V-shaped windows 82 and 84 of the mask at the front of the instrument, whilst the diode D6 receives no light at all.

The masking of the upper and lower regions of the lens 154 at 162 and 164 serves to cut out unwanted light and reduce reflections so as to more precisely obtain the differential illumination condition previously described with regard to photodiodes D5, D6 and D7.

Figure 16:
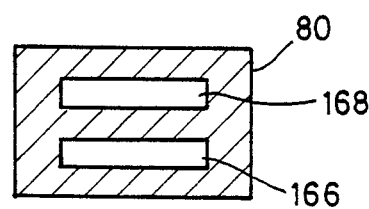
FIG. 16 is a plan view of the half silvered semireflecting mirror located to the rear of the puff tube.

A further improvement in cutting down unwanted light transmission and unwanted reflectance is demonstrated in FIG. 16 in which it will be noted that the semireflecting mirror 80 is masked by an opaque material except in the region of two windows 166 and 168 which serve to allow through light from the two generally V shaped windows in the original mask associated with the inspection lens assembly 18.

Figure 14:
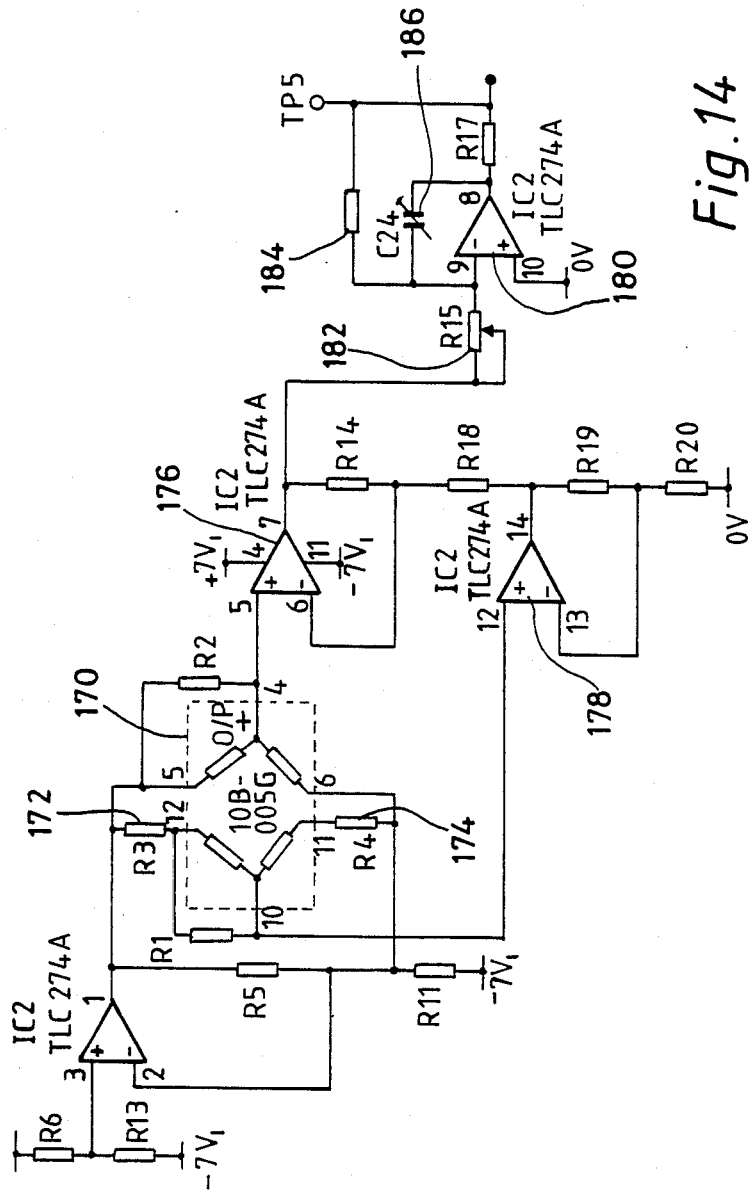
FIG. 14 is a circuit diagram of part of the signal processing circuit associated with the tonometer and illustrates the mode of adjustment to effect calibration.

FIG. 14 shows part of the circuit diagram of the analogue signal amplifying circuits associated with the pressure transducer located under the cover 52 on the printed circuit board 50. The pressure transducer is denoted by the dotted outline 170 and is in the form of a Wheatstone bridge with external resistors 172 and 174. The out of balance signal from the bridge is supplied to the two non-inverting inputs of a pair of differential amplifiers 176 and 178. The two outputs are summed to provide an input to the inverting input of a differential amplifier 180 via a series resistor 182 whose value can be varied. Feedback is provided by means of a high resistance 184 and a capacitor 186 whose value can be selected and/or is adjustable.

Adjustment of the value of resistor 182 alters the gain of the amplifier whilst selection and/or adjustment of the value of the capacitor 186 alter the time constant of the circuit and therefore rise time in response to a step input signal.

The gain of the amplifier 180 may of course be adjusted by varying the value of the feedback resistor 184 but since this may have an effect on the time constant of the circuit, it is considered more preferable that the gain should be adjusted by varying the input resistor 182 instead.

Adjustment of the value of resistor 182 and possibly the value of the capacitor 186 may be used during the calibration of the instrument, the procedure for which will be described later.

Figure 15:
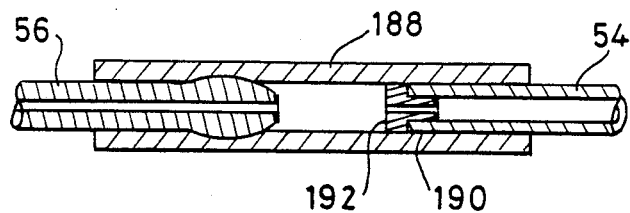
FIG. 15 is a cross-sectional view to an enlarged scale through part of the air supply line feeding to the pressure transducer in FIG. 6.

A further calibration adjustment is illustrated in FIG. 15. This illustrates diagrammatically the join between the tube 54 and the outlet pipe 56 from the plenum chamber. This is effected by means of a sleeve 188 which is fitted over the end of the tube 56 and over the end of the tube 54. The resistance to air flow is adjustable by inserting into the inboard end of the tube 54 a small restrictor in the form of an accurately bored sleeve 190 having a larger diameter head 192 which prevents the latter from passing completely into the tube 54. By selecting the length and diameter of the bore so different resistance to flow of air into the tube 54 can be achieved. The supply of air to the pressure transducer 170 below the cover 52 in FIG. 7, can thus be controlled so that the changes of electrical signal from the transducer faithfully follow changes of pressure in the air pulses leaving the tube 108.

Figure 17:
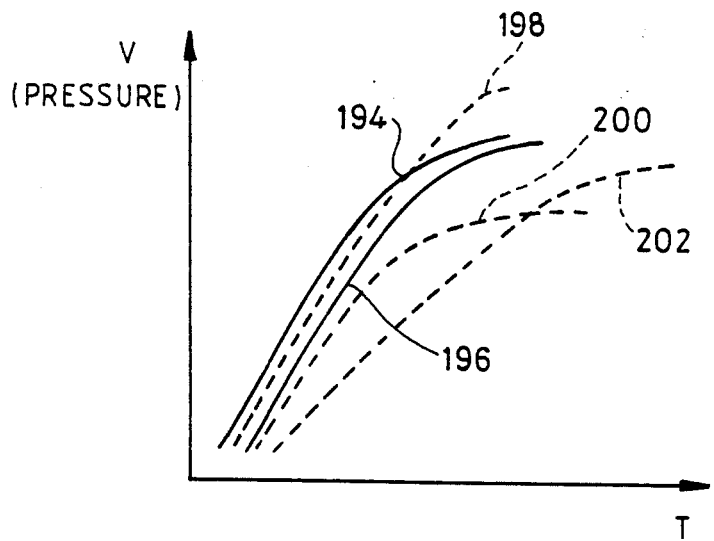
FIG. 17 illustrates the time-pressure traces obtained on a double beam storage oscilloscope during a calibration procedure on an instrument embodying the invention.

FIG. 17 illustrates graphically at 194 the change of voltage with respect to time which is obtained by directing an air pulse from the instrument towards a calibrated pressure transducer (not shown) and associated circuits for converting the pressure transducer response into an electrical signal the value of which is plotted at 194. This curve is denoted by reference numeral 194. The second curve in FIG. 17 denoted by reference numeral 196 illustrates the corresponding electrical signal voltage obtained from the output of amplifier 180 (FIG. 14) of the instrument which is supplying the air pulse. It will be seen that the second curve 196 is displaced by a small increment of time from the curve 194 and this time displacement can be increased or decreased by varying the size of the bore in the restrictor 190 of FIG. 15.

Other curves are denoted at 198 and 200. In the former case the gain of amplifier 180 has been set too high whilst in the case of curve 200, the gain has been set too low.

A further curve 202 is shown which corresponds to a further incorrect setting where a restrictor having a very small diameter has been employed which has caused the slope of the straight line section curve to fall away from the desired slope. Whilst the amplitude control 182 has been clearly set correctly, it is necessary to increase the response time of the amplifier 180 so as to enable the fall off in response due to the small restrictor to be compensated by altering the time constant of the amplifier circuit as by selecting a smaller value for the capacitor 186.

Curve 196 illustrates a close approximation to the desired calibration where the transducer circuit faithfully reproduces an electrical signal relating to pressure which closely corresponds to that produced from the test transducer against which the air pulse is applied.

The preferred method of calibration involves the following steps:

An instrument such as shown in FIG. 1 is set up a fixed distance away from a pressure transducer whose output signal for an applied pressure pulse has been calibrated so that the response curve closely follows that of a standard Goldmann instrument. The two curves shown in FIG. 17 at 194 and 196 are obtained by using a double beam storage oscilloscope which is set to simultaneously plot the instantaneous signal values relating to pressure as produced by the analogue circuit of FIG. 14 in the instrument under test and the analogue circuits responsive to the external calibrated pressure transducer against which the air impulses are projected. The plot of voltage is against the time duration of a single pulse. The traces are initiated at the beginning of the pulse when the air valve is operated.

A comparison of the two curves determines what adjustment if any is required so as to bring curve 196 as close as possible to conform to curve 194. Repeated tests may be performed by causing the instrument to fire as many times as is required, adjustments being made to the value of resistor 182, and if necessary capacitor 186, until the desired curve fit is obtained.

In general the optimum size for the restrictor is determined before any adjustments are made to the amplitude and/or slope of the curve.

We claim:

1. A tonometer for measuring the intra-ocular pressure of an eye in which a pulse of fluid is projected towards the cornea of the eye to distort the corneal surface by the pressure of the pulse, the distortion in the corneal surface being detected by a change in the reflection of light directed onto the cornea comprising:

(1) a fluid delivery system leading to an outlet through which the fluid pulse is applied to the cornea,
   (2) a branch in the fluid delivery system which leads to a pressure measuring chamber,
   (3) a transducer in the chamber which produces an electrical output signal whose value depends on the pressure in said branch,
   (4) a fluid flow restrictor removably located in the branch leading to the transducer, said restriction being selectable to provide selectable flow restrictions in said branch so as to correlate said electrical output signal from said transducer to the pressure of the fluid pulse delivered by said fluid delivery system, and
   (5) signal processing coupled to said transducer so as to receive said electrical output signal means the gain and rise time of which are adjustable, to enable the electrical signal output of the processing means to be adjusted so as to effect calibration of the tonometer when a selected restrictor is in place.

2. A tonometer as set forth in claim 1 wherein the signal processing means comprises an analogue amplifier the gain and time constant of which are adjustable, wherein adjustment of the gain enables the amplitude of the output signal to be adjusted and variation of the time constant enables the rise time of the output signal to be adjusted.

3. A tonometer as set forth in claim 1 wherein the fluid delivery system includes a housing having, at one end an apertured lens comprising the said outlet for the fluid pulses, inlet means to which fluid under pressure can be supplied when a pulse is required, and a connection for the said branch leading to the pressure measuring transducer.

4. A tonometer as set forth in claim 3 wherein the housing includes a first section which extends between the lens at the one end and a viewing eyepiece at the other and includes an optical focussing and reflecting system.

5. A tonometer as set forth in claim 4 wherein the housing includes a second section within which a source of illumination is located.

6. A tonometer as set forth in claim 4 wherein the housing includes a third section containing light detection means, the fluid inlet means, and the connection to the said branch leading to the pressure measuring transducer.

7. A tonometer as set forth in claim 6 a housing comprising said third section and a portion of the first section leading from the third section to the apertured lens, is separated from the remainder of the housing by means of a semi-reflecting mirror fitted so as to create a fluid-tight seal between the said first housing part and the remainder of the housing.

8. A tonometer as set forth in claim 3 wherein a part of the wall of the housing is comprised of a printed circuit board forming a light tight seal with the housing, and pressure measuring transducer is mounted on a region of the printed circuit board which communicates directly with the interior of the housing.

9. A tonometer as set forth in claim 3 wherein the apertured lens comprises a pair of aligned centrally apertured plano-convex lenses, a tube forming part of the fluid delivery system extends through the aligned apertures in the lenses, and a mask which defines two opposed V-shaped windows on opposite sides of said tube, to determine the shape of the final image on the light detection means is formed on one of the plane surfaces of the lenses.

10. A tonometer as set forth in claim 9 wherein the mask comprises two slit like windows symmetrically arranged relative to the central opening and bounded by an opaque surround.

11. A method for calibration of a non-contact tonometer which has a pressure measuring transducer subject to fluid pressure delivered through a fluid path branched from an air delivery system, which in use of the instrument delivers fluid pressure pulses to be incident on the eye, and wherein the branched fluid path has a removably locatable fluid flow restrictors selectable to correlate the pressure of the fluid pressure pulse delivered by their delivery system with an electrical output signal produced by the measuring transducer, said method comprising the steps of:

locating the selection restriction and the branched fluid path;

positioning the instrument incorporating the selected restrictor and to be calibrated according to the output of the air delivery system a fixed distance from a test pressure transducer, which has previously been calibrated to produce output signals which are proportional to the pressure readings which would be obtained using a standard tonometer, as a reference, establishing electrical connections whereby the output signals from the test transducer and from the signal processing means of the tonometer under test would be supplied to a double beam oscilloscope having signal storage facilities;

during the release of a single pulse of air from the instrument under test, simultaneously plotting the instantaneous electrical signal values produced by analog circuits coupled with the pressure transducer within the instrument under test and analog signal values from said test transducer;

comparing the two curves so obtained on said oscilloscope and adjusting at least one of the gain and time constant of the signal processing means of the instrument under test, so as to correct the curve produced by the signals from the instrument under test, so as to approximate the curve from said test transducer; and repeating the release of a single pulse of air towards the test transducer and the comparison adjustment steps until a desired level of identity between the pressure/time curves is obtained.

* * * * *